United States Patent
Zergiebel

(10) Patent No.: US 12,350,000 B2
(45) Date of Patent: Jul. 8, 2025

(54) COUPLING SURGICAL INSTRUMENTS TO ROBOTIC SURGICAL SYSTEMS

(71) Applicant: Covidien LP, Mansfield, MA (US)

(72) Inventor: Earl Zergiebel, Guilford, CT (US)

(73) Assignee: Covidien LP, Mansfield, MA (US)

( * ) Notice: Subject to any disclaimer, the term of this patent is extended or adjusted under 35 U.S.C. 154(b) by 1076 days.

(21) Appl. No.: 17/327,994

(22) Filed: May 24, 2021

(65) Prior Publication Data

US 2021/0275268 A1 Sep. 9, 2021

Related U.S. Application Data

(63) Continuation of application No. 16/082,007, filed as application No. PCT/US2017/020401 on Mar. 2, 2017, now Pat. No. 11,020,195.
(Continued)

(51) Int. Cl.
*A61B 34/00* (2016.01)
*A61B 17/00* (2006.01)
(Continued)

(52) U.S. Cl.
CPC ........ *A61B 34/71* (2016.02); *A61B 17/00234* (2013.01); *A61B 34/37* (2016.02);
(Continued)

(58) Field of Classification Search
CPC ......... A61B 34/30; A61B 34/37; A61B 34/71; A61B 2017/00477; A61B 2034/305;
(Continued)

(56) References Cited

U.S. PATENT DOCUMENTS 5,141,448 A 8/1992 Mattingly et al.
5,372,464 A 12/1994 Bureller
(Continued)

FOREIGN PATENT DOCUMENTS

CN 102014759 A 4/2011
CN 102171006 A 8/2011
(Continued)

OTHER PUBLICATIONS

Chinese Office Action for application No. 201780014344X dated Sep. 1, 2020 with English Translation.
(Continued)

*Primary Examiner* — Majid Jamialahmadi
(74) *Attorney, Agent, or Firm* — Carter, DeLuca & Farrell LLP

(57) ABSTRACT

A robotic surgical system includes a surgical instrument, a robotic arm, and a coupler assembly. The surgical instrument defines a longitudinal axis therethrough and supports an end effector on a free distal end portion of the surgical instrument. The robotic arm includes segments that are movably coupled together by joints. A first joint has at least two degrees of freedom for positioning the surgical instrument relative to a patient. The coupler assembly removably couples the surgical instrument to the robotic arm. The coupler assembly is positioned to enable the surgical instrument to rotate about the longitudinal axis and relative to the robotic arm.

10 Claims, 6 Drawing Sheets

Related U.S. Application Data

(60) Provisional application No. 62/303,613, filed on Mar. 4, 2016.

(51) Int. Cl.
*A61B 34/37* (2016.01)
*A61B 90/50* (2016.01)
*A61B 34/30* (2016.01)

(52) U.S. Cl.
CPC .... *A61B 90/50* (2016.02); *A61B 2017/00477* (2013.01); *A61B 2034/305* (2016.02)

(58) Field of Classification Search
CPC .............. A61B 34/70; A61B 2034/306; A61B 2034/715; A61B 90/50
See application file for complete search history.

(56) References Cited

U.S. PATENT DOCUMENTS

| | | | |
|---|---|---|---|
| 5,653,605 A | 8/1997 | Woehl et al. | |
| 5,741,084 A | 4/1998 | Del Rio | |
| 6,226,068 B1 | 5/2001 | Arcykiewicz et al. | |
| 6,231,565 B1* | 5/2001 | Tovey | A61B 34/30 606/1 |
| 6,921,283 B2 | 7/2005 | Zahlit | |
| 7,104,826 B2 | 9/2006 | Zahlit et al. | |
| 7,914,311 B1 | 3/2011 | Gallusser et al. | |
| 8,840,628 B2 | 9/2014 | Green et al. | |
| 11,020,195 B2 | 6/2021 | Zergiebel | |
| 2012/0116416 A1 | 5/2012 | Neff et al. | |
| 2014/0276720 A1 | 9/2014 | Parihar et al. | |
| 2015/0148816 A1 | 5/2015 | Govari et al. | |
| 2016/0001448 A1* | 1/2016 | Rothfuss | B25J 15/0028 901/31 |
| 2017/0050011 A1 | 2/2017 | Zergiebel | |
| 2019/0000706 A1 | 1/2019 | Hares | |
| 2020/0164528 A1 | 5/2020 | Giesen | |

FOREIGN PATENT DOCUMENTS

| | | |
|---|---|---|
| CN | 105208962 A | 12/2015 |
| EP | 2599447 A2 | 6/2013 |
| WO | 2015088647 A1 | 6/2015 |

OTHER PUBLICATIONS

Extended European Search Report issued in corresponding Appl. No. 17760792.6 dated Oct. 2, 2019.
Chinese Office Action for application No. 201780014344X dated Jan. 5, 2021 with English translation.
Communication Pursuant to Article 94(3) EPC issued in corresponding European Application No. 17 760 792.6 dated Jul. 3, 2023, 5 pages.

* cited by examiner

COUPLING SURGICAL INSTRUMENTS TO ROBOTIC SURGICAL SYSTEMS

CROSS REFERENCE TO RELATED APPLICATIONS

This application is a Continuation of U.S. patent application Ser. No. 16/082,007, filed Sep. 4, 2018, which is a U.S. National Stage Application filed under 35 U.S.C. § 371(a) of International Patent Application Serial No. PCT/US2017/020401, filed Mar. 2, 2017, which claims the benefit of U.S. Provisional Patent Application No. 62/303,613, filed Mar. 4, 2016, the entire contents of each of which are hereby incorporated by reference herein.

BACKGROUND

Robotic surgical systems were widespread in minimally invasive medical procedures. As with surgical procedures performed manually by a surgeon, robotic surgical systems required the use of various surgical instruments in order to successfully complete the procedure. These surgical instruments were operatively connected to a robotic arm and included several connecting features that enabled the surgeon to control the surgical instrument in a precise manner. These connections involved the complex interconnection of mechanical, electrical, and/or pneumatic features. The particular procedure being performed often involved frequent installation and/or removal of one or more surgical instruments. Thus, in certain instances, instrument exchange was cumbersome and time consuming.

Accordingly, there is a need for new coupling devices and methods that enable easy, quick, and reliable removal and/or installation of surgical instruments to robotic surgical systems.

SUMMARY

The present disclosure describes robotic devices, systems, and methods that demonstrate a practical approach to meeting the performance requirements and overcoming the usability challenges associated with surgical instrument exchange. In general, the present disclosure describes robotic surgical systems that include surgical instruments for connection to robotic arms via coupler assemblies. The presently described coupler assemblies provide removal and/or installation of the surgical instruments to the robotic arms with stationary and rotation hubs that removably couple to one another. The stationary hub is secured to the robotic arm or to the surgical instrument (or component thereof) while the rotation hub, which includes a rotation member and a support member, is secured to the other of the robotic arm of the surgical instrument (or component thereof). Rotation member of rotation hub and stationary hub each include complementary mating features that are selectively engageable with one another. The coupling and/or decoupling of stationary and rotation hubs can be effectuated by merely rotating rotation member of rotation hub relative to support member of rotation hub to engage and/or disengage the complementary mating features. As the complementary mating feature engage and/or disengage, the surgical instrument can be easily, quickly, and reliably installed and/or removed to/from the robotic arm.

According to one aspect, a coupler assembly for selective connection of a surgical instrument to a robotic arm is provided. In another aspect, a robotic surgical system including a surgical instrument, robotic arm, and a coupler assembly is provided.

The coupler assembly includes a stationary hub and a rotation hub. The stationary hub has a first mating feature and is secured to a first one of the surgical instrument and the robotic arm. The rotation hub includes a support member and rotation member mounted on the support member. The support member is secured to a second one of the surgical instrument and the robotic arm. The rotation member is rotatable relative to the support member between a first state and a second state. The rotation member has a second mating feature that releasably couples to the first mating of the stationary hub as the rotation member rotates relative to the stationary hub.

In embodiments, the first mating feature of the stationary hub includes a boss and the second mating feature of the rotation hub includes a slot defined in the rotation member. The boss is receivable within the slot to couple the stationary hub to the rotation hub. The rotation member may include an outer surface that extends between top and bottom surfaces. The slot may extend diagonally around the outer surface of the rotation member and open through the bottom surface of the rotation member. The rotation member may include a ledge that extends into the slot. The ledge is positioned to engage the boss while the rotation member is in the first state. The boss is separable from the ledge as the rotation member moves toward the second state.

The coupler assembly may further include a bias washer interposed between the rotation member and the support member of the rotation hub. The rotation member may include an inner surface having an inner flange extending radially inwardly from the inner surface. The support member may have an outer surface and an outer flange extending radially outwardly from the outer surface of the support member. The bias washer may be supported on the inner flange of the rotation member and in contact with the outer flange of the support member. In certain embodiments, the bias washer includes a Bellville washer, a curved disk spring, a wave washer, or combinations thereof.

In embodiments, the rotation member includes a prong extending therefrom and the support member includes an outer flange extending radially outwardly from an outer surface of the support member. The outer flange may define a second slot positioned to receive the prong of the rotation member. The second slot may be arcuate.

In certain embodiments, the rotation member includes at least one second prong. Each prong defines a groove therein such that the second prong and the grooves formed therein are positioned to receive a retention ring therein that inhibits axial movement of the rotation member relative to the support member.

The coupler assembly may further include a biasing element positioned within the second slot of the outer flange and in contact with the prong. The biasing element may be configured to compress as the prong translates through the second slot while the rotation member rotates relative to the support member. The biasing element biases the rotation element toward the first state.

Further details and aspects of exemplary embodiments of the present disclosure are described in more detail below with reference to the appended figures.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
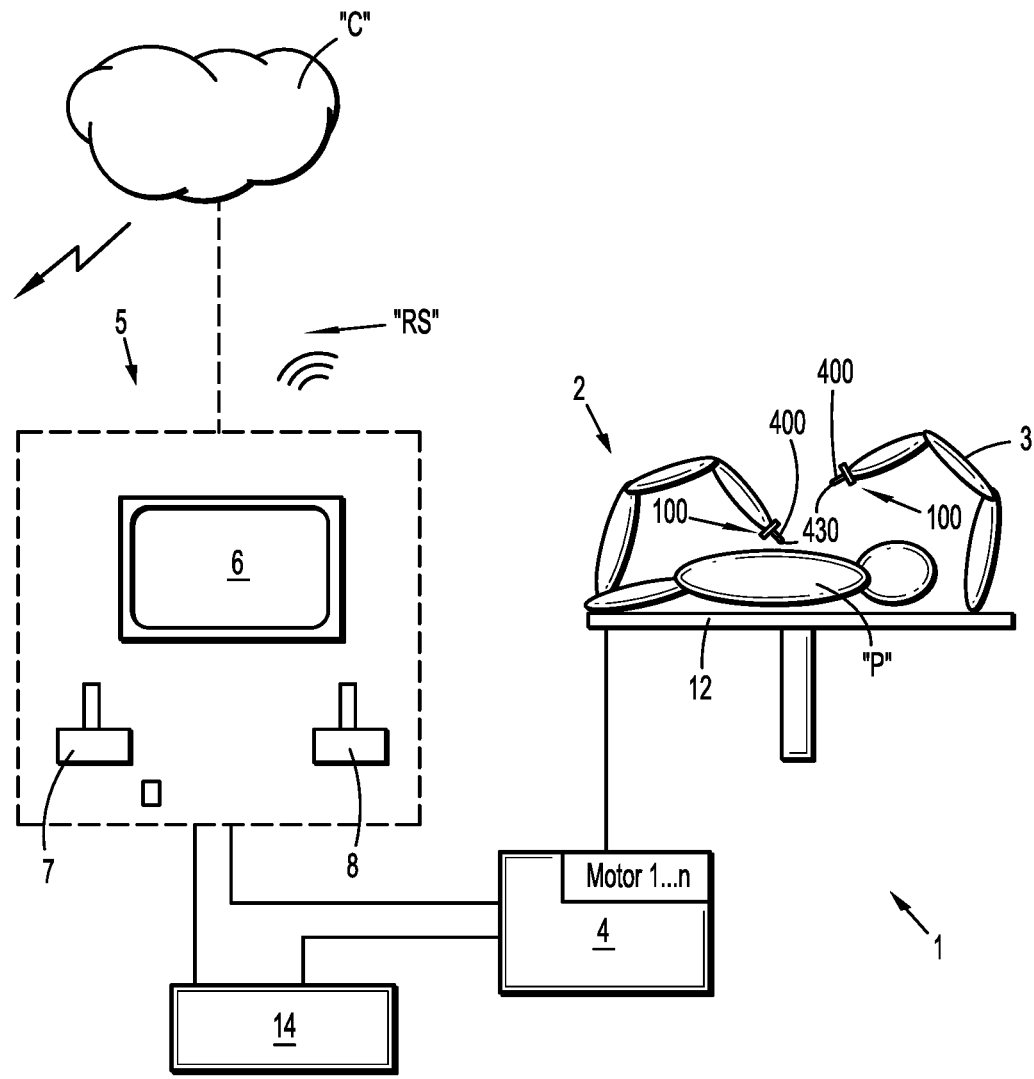
FIG. 1 is a schematic illustration of a robotic surgical system in accordance with the present disclosure.

Embodiments of the present disclosure are described in detail below with reference to the drawings in which like reference numerals designate identical or corresponding elements in each of the several views. As used herein, the term "clinician" refers to a doctor, a nurse or any other care provider and may include support personnel. Throughout this description, the term "proximal" will refer to the portion of the device or component thereof that is closer to the clinician and the term "distal" will refer to the portion of the device or component thereof that is farther from the clinician. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

With reference to FIG. 1, a robotic surgical system in accordance with the present disclosure is generally identified as reference numeral 1. Robotic surgical system 1 includes a plurality of robotic arms 2, 3, a controller or control device 4, and an operating console 5 operably coupled with control device 4. Operating console 5 includes a display device 6, which is set up in particular to display three-dimensional images, and manual input devices 7 and 8, by means of which a clinician (not shown), for example, a surgeon, is able to telemanipulate robotic arms 2, 3. Each of the plurality of robotic arms 2, 3 includes a plurality of segments 3x, each of which are connected through joints 3y to enable relative movement between the segments 3x and/or joints 3y.

Figure 2A:
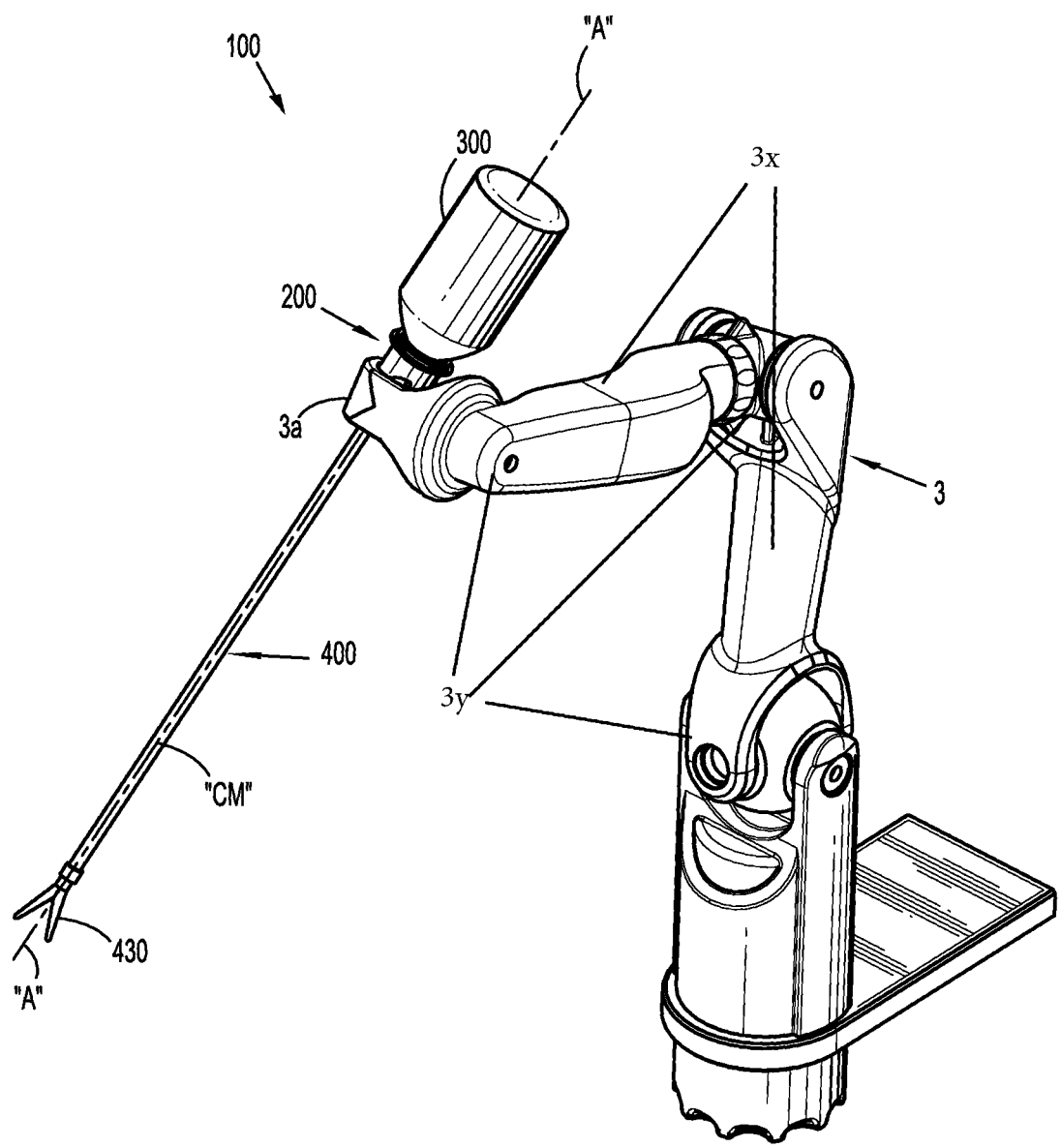
FIG. 2A is a perspective view of a robotic arm of the robotic surgical system of FIG. 1 with a surgical instrument of the robotic surgical system shown mounted to the robotic arm.
Figure 2B:
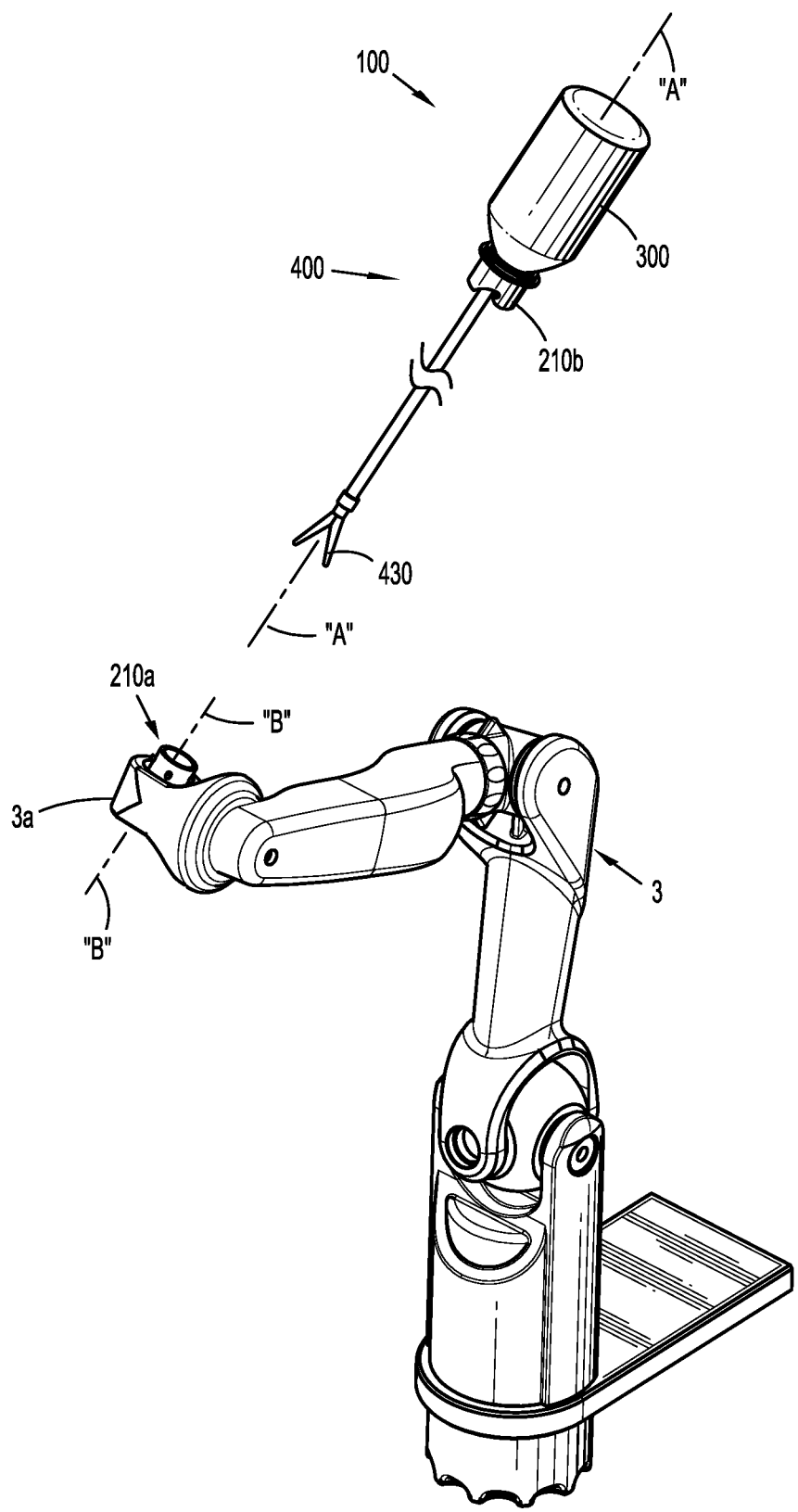
FIG. 2B is a perspective view illustrating the surgical instrument of FIG. 2A shown separated from the robotic arm of FIG. 2A.

Referring also to FIGS. 2A and 2B, robotic surgical system 1 includes a surgical instrument 100 that releasably couples to a mount or mounting member 3a of robotic arms 2, 3 via a coupler assembly 200, as will be discussed in further detail below. Surgical instrument 100 includes an instrument drive unit 300 and a surgical instrument 400 that define a longitudinal axis "A" extending therethrough. In some embodiments, instrument drive unit 300 is fixedly secured to surgical instrument 400. In certain embodiments, surgical instrument 400 is detachably coupled to instrument drive unit 300. Surgical instrument 400 includes an end effector 430 disposed at a distal end thereof that is operatively coupled to instrument drive unit 300 by one or more connector members "CM" (e.g., cables, rod, belts, chains, etc., or combinations thereof) to enable end effector 430 to perform one or more functions.

With reference to FIG. 1, robotic arms 2, 3 may be driven by electric drives (not shown) that are connected to control device 4. Control device 4 (e.g., a computer) is set up to activate the drives such that surgical instrument 400 (including end effector 430), robotic arms 2, 3, and instrument drive units 300 (FIG. 2A) cooperate to execute a desired movement according to a movement defined by operation of manual input devices 7, 8. It is contemplated that control device 4 may activate the drives by means of a computer program. Control device 4 may also be set up in such a way that it regulates movement of robotic arms 2, 3 and/or of the drives.

Robotic surgical system 1 is configured for use on a patient "P" lying on a surgical table 12 to be treated in a minimally invasive manner by surgical instruments such as surgical instrument 400. Robotic surgical system 1 may also include more than two robotic arms 2, 3. The additional robotic arms are likewise connected to control device 4 and are telemanipulatable by operating console 5. One or more additional surgical instruments 100 and/or surgical instruments 400 may be attached to any additional robotic arms 2, 3.

Control device 4 may control a plurality of motors (Motor 1 . . . n) with each motor configured to drive a pushing and/or a pulling of one or more of connector members "CM" (see FIG. 2A) coupled to end effector 430 of surgical instrument 400. In use, as connector members "CM" are pushed and/or pulled, connector members "CM" effect operation and/or movement of end effector 430 of surgical instrument 400. It is contemplated that control device 4 coordinates activation of the various motors (Motor 1 . . . n) to coordinate a pushing and/or a pulling motion of one or more of connector members "CM" in order to coordinate an operation and/or movement of one or more end effectors 430 of robotic surgical system 1.

Control device 4 can include any suitable logic control circuit adapted to perform calculations and/or operate according to a set of instructions. Control device 4 can be configured to communicate with a remote system "RS," either via a wireless (e.g., Wi-Fi™, Bluetooth®, LTE™, etc.) and/or wired connection. Remote system "RS" can include data, instructions and/or information related to the various components, algorithms, and/or operations of robotic surgical system 1. Remote system "RS" can include any suitable electronic service, database, platform, cloud "C," or the like. Control device 4 may include a central processing unit operably connected to memory. The memory may include transitory type memory (e.g., RAM) and/or non-transitory type memory (e.g., flash media, disk media, etc.). In some embodiments, the memory is part of, and/or operably coupled to, remote system "RS."

Control device 4 can include a plurality of inputs and outputs for interfacing with the components of robotic surgical system 1, such as through a driver circuit. Control device 4 can be configured to receive input signals and/or generate output signals to control one or more of the various components (e.g., one or more motors) of robotic surgical system 1. The output signals can include, and/or can be based upon, algorithmic instructions which may be preprogrammed and/or input by a user. Control device 4 can be configured to accept a plurality of user inputs from a user interface (e.g., switches, buttons, touch screen, etc. of operating console 5) which may be coupled to remote system "RS."

A database 14 can be directly and/or indirectly coupled to control device 4. Database 14 can be configured to store pre-operative data from living being(s) and/or anatomical atlas(es). Database 14 can include memory which can be part of, and/or or operatively coupled to, remote system "RS." Reference may be made to U.S. Patent Publication No. 2012/0116416, filed on Nov. 3, 2011, entitled "Medical Workstation," the entire content of which is incorporated herein by reference, for a detailed discussion of the construction and operation of robotic surgical system 1. Reference may also be made to International Application No. PCT/US2014/61329, filed on Oct. 20, 2014, entitled "Wrist and Jaw Assemblies for Robotic Surgical Systems," the entire content of which is incorporated herein by reference, for a detailed description of the construction and/or operation of various components of a robotic surgical system.

Figure 3:
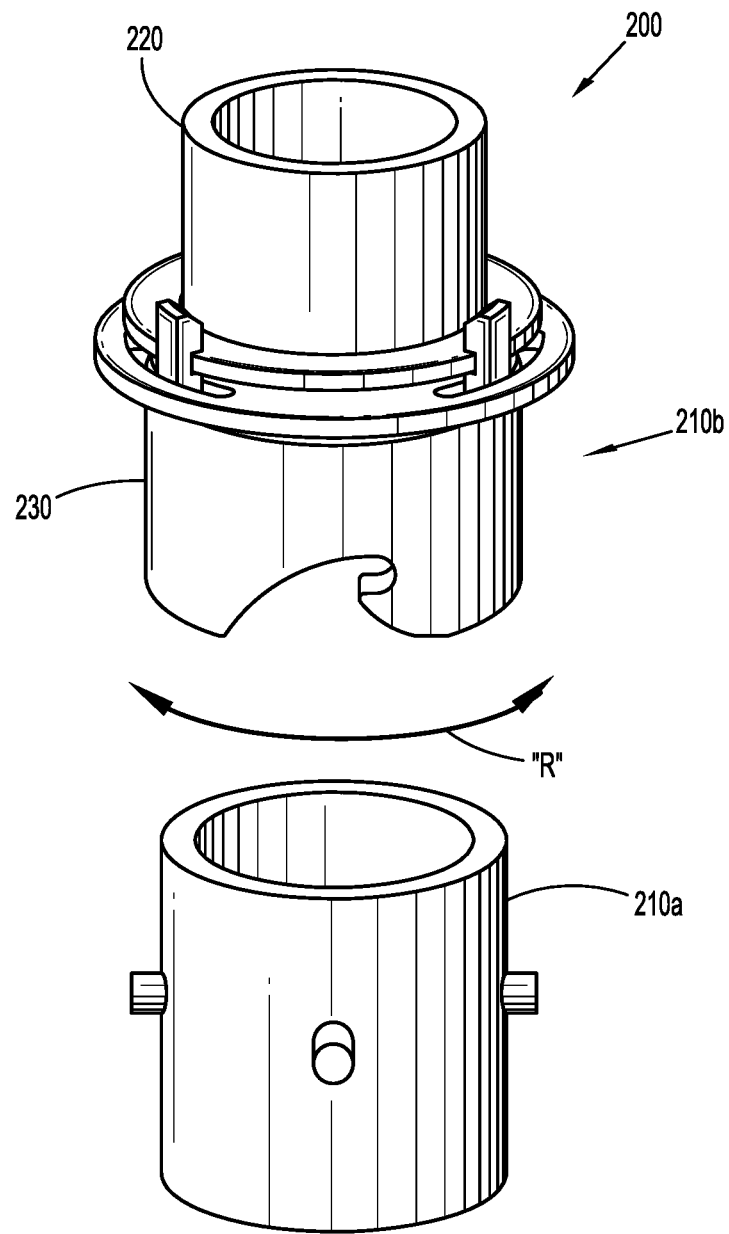
FIG. 3 is a perspective view, with parts separated, of a coupler assembly of the robotic surgical system of FIG. 1.

Referring to FIGS. 2A, 2B, and 3, coupler assembly 200 generally includes a first or stationary hub 210a, and a second or rotation hub 210b that releasably couples to stationary hub 210a. It is contemplated that coupler assembly 200, and/or components thereof, may be formed from any suitable material capable of being used in a surgical environment such as stainless steel, cobalt chrome, ceramics, polymers, or the like. Using any suitable fastening techniques such as friction fit, welding, adhesives, and/or the like, coupler assembly 200, and/or components thereof, can be secured to mount 3a of robotic arm 3 and/or to surgical instrument 100. For example, stationary hub 210a can be secured to mount 3a while rotation hub 210b is secured to surgical instrument 100, or vice versa, such that surgical instrument 100 can be selectively coupled and/or uncoupled to robotic arm 3.

Figure 4A:
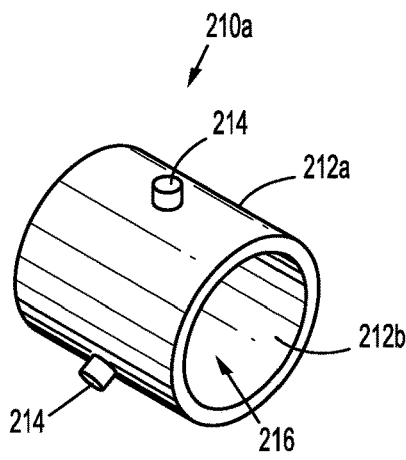
FIG. 4A is a side, perspective view of a stationary hub of the coupler assembly of FIG. 3.
Figure 4B:
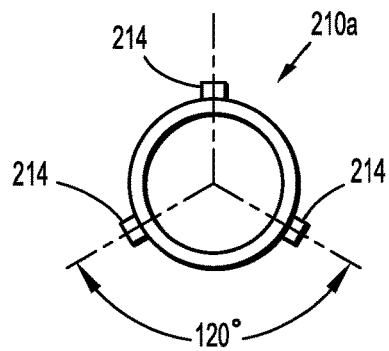
FIG. 4B is a top view of the stationary hub of FIG. 4A.

Referring to FIGS. 4A and 4B, stationary hub 210a of coupler assembly 200 may have any suitable configuration such as cylindrical, square, rectangular, hexagonal, or the like. Stationary hub 210a includes an outer surface 212a and an inner surface 212b. Outer surface 212a includes mating features 214 such as lugs or bosses that extend radially outward therefrom and inner surface 212b defines a throughbore 216 that extends axially through stationary hub 210. Mating features 214 may be formed uniformly with stationary hub 210a (e.g., a machined feature). In embodiments, mating features 214 may be separate bodies secured within respective counterbores or throughbores (not shown) defined within outer surface 212a using any suitable fastening techniques such as fastening, friction fit, welding, adhesives, and/or the like. Although generally shown as including three mating features 214 disposed thereon, it is contemplated that stationary hub 210a may include any suitable number of mating features 214. Mating features 214 are disposed in spaced relation to one another to enable rotation hub 210b (FIG. 5) to selectively couple thereto, as will be described in further detail below. Mating features 214 may be placed at predetermined locations about outer surface 212a of stationary hub 210a. For example, as seen in FIG. 4B, mating features 214 may be disposed at equidistant radial locations such as every 120 degrees or every 90 degrees in the case of three and four mating features 214, respectively.

Figure 5:
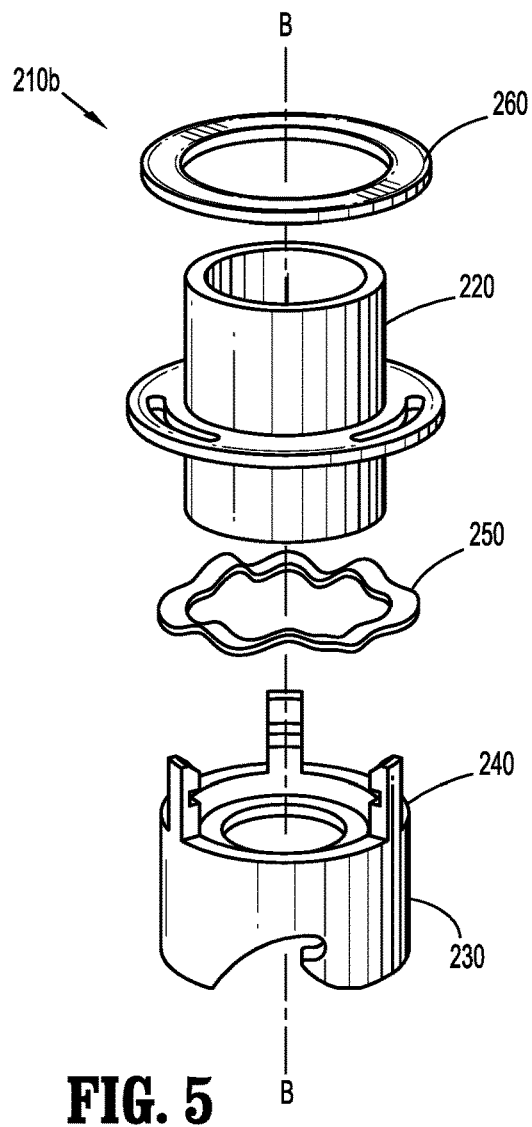
FIG. 5 is a perspective view, with parts separated, of a rotation hub of the coupling assembly of FIG. 3.

With reference to FIG. 5, rotation hub 210b includes a support member 220, a rotation member 230, biasing elements 240, a bias washer 250, and a retention ring 260. The components of rotation hub 210b are stacked along a longitudinal axis "B." Biasing elements 240 may include a coil spring or the like. Bias washer 250 may be any suitable biasing washer such as a Bellville washer, curved disk spring, wave washer, or the like. Retention ring 260 may include any suitable retention ring such as a washer, circlip, spiral retention ring, or the like.

Figure 6A:
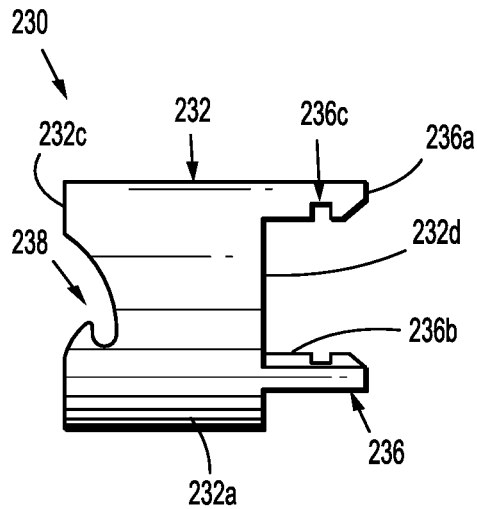
FIG. 6A is a side view of a rotation member of the rotation hub of FIG. 5.
Figure 6B:
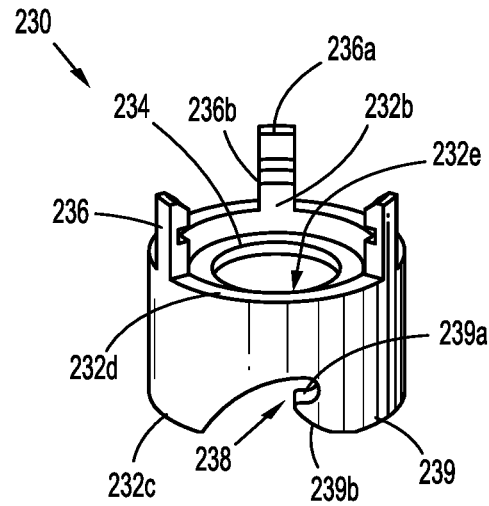
FIG. 6B is a perspective view of the rotation member of FIG. 6A.

As illustrated in FIGS. 6A and 6B, rotation member 230 of rotation hub 210b may have a body 232 with any suitable configuration such as cylindrical, square, rectangular, hexagonal, or the like. Body 232 includes an outer surface 232a, an inner surface 232b, a lower surface 232c, and an upper surface 232d. Inner surface 232b defines a passage 232e therethrough and includes an inner flange 234 extending radially outward from the inner surface 232b to support bias washer 250.

Prongs 236 extend from upper surface 232c of body 232, with each prong 236 defining to a tooth 236a. Although rotation member 230 is shown with three prongs 236, it is contemplated that any suitable number of prongs 236 may be disposed on upper surface 232c of rotation member 230. Prongs 236 may be arranged on upper surface 232c of rotation member 230 at predetermined locations therealong. For example, adjacent prongs 236 may be disposed 120 degrees apart. In some embodiments, spacing of prongs 236 may be dependent upon the number of prongs 236 disposed on upper surface 232c (e.g., 180 degrees for two prongs 236, 90 degrees for three prongs 236, etc.). A groove 236c is defined in an inner surface 236b of each prong 236 that functions to releasably retain retention ring 260 while retention and rotation members 220, 230 are joined together to inhibit separation of retention and rotation members 220, 230. Collectively, grooves 236c of prongs 236 define an annular channel 236d within which retention ring 260 is supported.

Prongs 236 may have a resilient configuration that enables support member 220 to support retention ring 260 while retention and rotation members 220, 230 are coupled together. For example, prongs 236 may be deflected outwardly from an initial condition to enable retention ring 260 to be received within annular grooves 236c of prongs 236. Prongs 236 are biased to return to the initial condition to maintain retention ring 260 within grooves 236c of prongs 236.

Mating features 238 such as diagonal slots are defined through inner and outer surfaces 232a, 232b of rotation member 230 at predetermined locations around body 232 of rotation member 230. Each mating feature 238 extends vertically from lower surface 232c of rotation member 230 and is further defined by a protrusion or ledge 239 that extends into mating feature 238. Ledge 239 has a retaining surface 239a that is parallel with upper surface 232d of body 232 and an angled side surface 239b that intersects retaining surface 239a. Mating features 238 are positioned on body 232 of rotation member 230 to slidingly receive corresponding bosses 214 (see FIGS. 4A and 4B) of stationary hub 210a as rotation member 230 of rotating hub 210b is rotated relative to stationary hub 210a in a bayonet-type fashion.

Figure 7A:
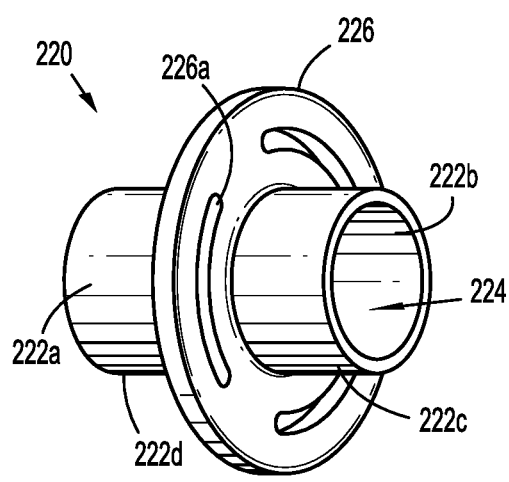
FIG. 7A is a side, perspective view of a support member of the rotation hub of FIG. 5.
Figure 7B:
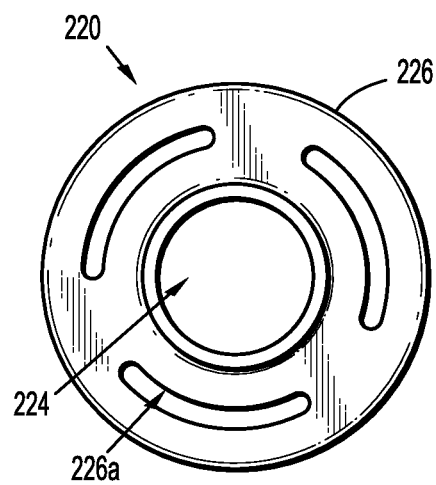
FIG. 7B is a top view of the support member of FIG. 7A.

With reference to FIGS. 7A and 7B, support member 220 of rotation hub 210b has a generally cylindrical configuration, although other suitable configurations are contemplated, such as square, rectangular, octagonal, and/or the like. In general, the configuration of support member 220 is complementary to that of bore 232e of rotation member 230 (see FIGS. 6A and 6B) such that support member 220 may be received within bore 232e of rotation member 230.

Support member 220 includes an outer surface 222a and an inner surface 222b. Inner surface 222b defines a lumen 224 that extends axially through support member 220. A flange 226 extends radially outwardly from outer surface 222a of support member 220 and may separate a length of support member 220 between an upper portion 222c and a lower portion 222d. Flange 226 may bisect upper and lower portions 222c, 222d and functions as a bearing surface that supports bias washer 250 when support member 220 is advanced within bore 232e of rotation member 230 such that bias washer 250 nests between inner flange 234 of rotation member 230 and flange 226 of support member 220 (see FIG. 5).

Flange 226 defines slots 226a therethrough that receive prongs 236 of rotation member 230 and support biasing elements 240 therein. Slots 226a may have a generally arcuate shape with a radius proportional to a radius of flange 226. Slots 226a are arranged at predetermined locations about flange 226. For example, slots 226a may be disposed at equidistant locations such as every 120 degrees, however, slots 226a are generally arranged in a complimentary configuration to that of prongs 236 of rotation member 230 (see FIGS. 6A and 6B). Slots 226a are positioned to enable prongs 236 to slidably translate through slots 226a as rotation member 230 is rotated relative to support member 220 and/or stationary hub 210a, as described in further detail below.

In operation, to attach surgical system 100 to one of robotic arms 2, 3, a clinician positions stationary and/or rotation hub 210a, 210b such that mating features 214 of stationary hub 210a are aligned with mating features 238 of rotation member 230. Stationary and rotation hubs 210a, 210b are then approximated until bosses 212 of stationary hub 210a are positioned within mating features 238 and secured against retaining surface 239a. As indicated by arrow "R" shown in FIG. 3, relative rotation between stationary and rotation hub 210a, 210b may facilitate reception of mating features 214 of stationary hub 210a within mating features 238 of rotation hub 210b. To facilitate reception of mating features 214 of stationary hub 210a within mating features 238 of rotation hub 210b, relative rotation between stationary and rotation hub 210a, 210b may involve rotating mount 3a of robotic arm 3 relative to surgical instrument 100 (or components thereof) and/or rotating surgical instrument 100 (or components thereof) relative to mount 3a. Additionally and/or alternatively, rotation member 230 of rotation hub 210b may be rotated relative to support member 220 to facilitate reception of mating features 214 of stationary hub 210a within mating features 238 of rotation hub 210b.

With rotation member 230 biased to an initial, unrotated state under spring force (a rotational biasing force), exerted by biasing members 240 against prongs 236, rotation of rotation member 230, as indicated by arrows "R" of FIG. 3, slides prongs 236 of rotation member 230 through slots 226a of support member 220 towards biasing elements 240, compressing biasing elements 240 from an extended state to a compressed state. Upon release of applied rotational forces acting on rotation member 230, to effectuate rotation thereof, the spring force of biasing elements 240, which is counter to the applied rotational forces, causes rotation member 230 to return to its initial, unrotated state.

Once stationary and/or rotation hub 210a, 210b are coupled together with rotation member 230 of rotation hub 210b disposed in its initial, unrotated state, mating features 214 of stationary hub 210a are secured against ledge 239 of rotation hub 210b under the spring force imparted by biasing members 240 of rotation hub 210b against prongs 236 of rotation hub 210b. Also while stationary and/or rotation hub 210a, 210b are coupled together in this position, bias washer 250 provides an axial biasing force against mating features 214 of stationary hub 210a to inhibit axial movement of rotation member 230 of rotation hub 210b with respect to stationary hub 210a along axis "A."

When an instrument exchange or removal is desired, rotation member 230 of rotation hub 210b can be rotated against the rotational biasing force of biasing elements 240 so as to compress biasing elements 240 as prongs 236 of rotation member 230 rotate along slots 226a of support member 220 as described above. As rotation member 230 is rotated, mating features 214 of stationary hub 210a separate from mating features 238 of rotation hub 210b, enabling stationary and rotation hubs 210a, 210b to separate for freeing surgical instrument 100 (and/or components thereof) from robotic arm 3. Surgical instrument 100 (and/or components thereof) can then be reinserted or replaced with a different surgical instrument 100 (and/or component thereof) similar to that described above as desired. For example, a different surgical instrument 100 may include a different end effector that functions differently than end effector 430 of surgical instrument 100 (e.g., an instrument that seals versus an instrument that fastens) to effectuate a different aspect of the surgical procedure.

In some embodiments, mating features 214, 238 of stationary and rotation hubs 210a, 210b are reversed such that stationary hub 210a defines mating features 238 and rotation hub 210b includes mating features 214. In certain embodiments, both of stationary and rotation hubs 210a, 210b include one or more mating features 214 and one or more mating features 238 such that corresponding mating features of stationary and rotation hubs 210a, 210b are positioned to align with its respect complementary mating feature on the other of the stationary and rotation hub 210a, 210b.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed:

1. A robotic surgical system, comprising:
   at least one surgical instrument having an instrument drive unit supported on a proximal end portion thereof, an elongated shaft that extends distally from the instrument drive unit, and an end effector secured to a distal end portion of the elongated shaft and operably connected to the instrument drive unit by a connector member for operating the end effector, the at least one surgical instrument defining a longitudinal axis that extends therethrough from the instrument drive unit to the end effector;
   a robotic arm including at least three segments that are movably coupled together by at least three joints, wherein at least a first joint of the at least three joints has at least two degrees of freedom such that the first joint can rotate in different directions about orthogonal axes defined through the first joint, at least two segments of the at least three segments and the at least three joints are movable to position the end effector relative to a patient; and a mounting member supported by the robotic arm and configured to be removably coupled to the at least one surgical instrument by a coupler assembly, the coupler assembly including:

a support member secured to the mounting member, the support member being tubular and having at least one first mating feature projecting radially outwardly for securing the at least one surgical instrument to the mounting member; and a rotation hub secured to the at least one surgical instrument, the rotation hub defining at least one diagonal slot extending proximally from a distal edge of the rotation hub, and is configured to receive the corresponding at least one first mating feature, whereby the rotation hub is selectively connectable to the support member via a bayonet-type connection, wherein, the at least one surgical instrument is rotatable about the longitudinal axis and relative to the mounting member when the at least one surgical instrument is coupled to the coupler assembly.

2. The robotic surgical system of claim 1, wherein the coupler assembly defines a throughbore that facilitates passage of the elongated shaft of the at least one surgical instrument through the mounting member.

3. The robotic surgical system of claim 2, wherein the support member of the coupler assembly is a first hub of the coupler assembly, wherein the first hub includes the at least one first mating feature, and wherein the first hub is stationary within the mounting member.

4. The robotic surgical system of claim 3, wherein the at least one first mating feature includes three bosses disposed radially about the first hub at equidistant radial locations.

5. The robotic surgical system of claim 4, wherein the rotation hub of the coupler assembly is a second hub of the coupler assembly, wherein the at least one diagonal slot defines at least one second mating feature, wherein the at least one second mating feature includes a second mating feature corresponding to each boss of the first hub.

6. A robotic surgical system, comprising:

a surgical instrument having a proximal end portion, an elongated shaft that extends distally from the proximal end portion and defines a longitudinal axis therethrough, and an end effector supported on a free distal end portion of the surgical instrument and secured to a distal end portion of the elongated shaft, the end effector including a first jaw member and a second jaw member;

a robotic arm including at least three segments that are movably coupled together by at least three joints, wherein at least a first joint of the at least three joints has at least two degrees of freedom, and wherein at least two segments of the at least three segments and the at least three joints cooperate to position the surgical instrument relative to a patient; and a coupler assembly that removably couples the surgical instrument to the robotic arm, the coupler assembly including:

a support member secured to a mounting member, the support member being tubular and having at least one first mating feature projecting radially outwardly for securing the at least one surgical instrument to the mounting member; and a rotation hub secured to the at least one surgical instrument, the rotation hub defining at least one diagonal slot extending proximally from a distal edge of the rotation hub, wherein the at least one each diagonal slot is configured to receive the at least one first mating feature, whereby the rotation hub is selectively connectable to the support member via a bayonet-type connection, whereby the surgical instrument is rotatable about the longitudinal axis defined through the elongated shaft and relative to robotic arm.

7. The robotic surgical system of claim 6, wherein the at least one first mating feature includes a boss.

8. The robotic surgical system of claim 7, wherein the at least one first mating feature includes three bosses disposed radially about the first hub at equidistant radial locations.

9. The robotic surgical system of claim 8, wherein the coupler assembly includes a prong and an outer flange, the outer flange defining a second slot positioned to receive the prong.

10. The robotic surgical system of claim 9, wherein the outer flange extends radially outward from an outer surface of the coupler assembly.

* * * * *